(12) United States Patent
Eichenberg

(10) Patent No.: US 12,263,114 B2
(45) Date of Patent: Apr. 1, 2025

(54) THERAPEUTIC DEVICE FOR ALLEVIATING A SEXUAL DYSFUNCTION AND METHOD OF MAKING THE SAME

(71) Applicant: David Eichenberg, Toledo, OH (US)

(72) Inventor: David Eichenberg, Toledo, OH (US)

( * ) Notice: Subject to any disclaimer, the term of this patent is extended or adjusted under 35 U.S.C. 154(b) by 147 days.

(21) Appl. No.: 17/491,875

(22) Filed: Oct. 1, 2021

(65) Prior Publication Data

US 2022/0104962 A1 Apr. 7, 2022

Related U.S. Application Data

(60) Provisional application No. 63/086,108, filed on Oct. 1, 2020.

(51) Int. Cl.
| | | |
|---|---|---|
| *A61F 5/41* | (2006.01) | |
| *B29C 39/02* | (2006.01) | |
| *B29C 39/44* | (2006.01) | |
| *B29K 83/00* | (2006.01) | |
| *B29L 31/00* | (2006.01) | |

(52) U.S. Cl.
CPC ............... *A61F 5/41* (2013.01); *B29C 39/02* (2013.01); *B29C 39/44* (2013.01); *A61F 2005/411* (2013.01); *A61F 2005/412* (2013.01); *B29K 2083/00* (2013.01); *B29L 2031/753* (2013.01)

(58) Field of Classification Search
CPC ............... A61F 5/41; A61F 2005/411; A61F 2005/412; A61F 2005/414; A61F 2005/415; A61H 19/32; A61H 19/40; A61H 19/44
See application file for complete search history.

(56) References Cited

U.S. PATENT DOCUMENTS

| | | | |
|---|---|---|---|
| 4,671,262 A * | 6/1987 | West | A61F 5/41 600/39 |
| 4,690,135 A | 9/1987 | Gerow | |
| 5,083,556 A | 1/1992 | Osborn | |
| 5,094,230 A | 3/1992 | Clark | |
| 5,127,396 A * | 7/1992 | McAllister | A61H 19/40 600/38 |
| 5,624,378 A | 4/1997 | Baldecchi | |
| 5,741,511 A | 4/1998 | Mahulikar | |
| 6,547,717 B1 * | 4/2003 | Green | A61H 19/44 600/38 |
| 9,314,396 B2 | 4/2016 | Smith | |
| 9,968,479 B2 | 5/2018 | Harkins, Jr. | |
| 11,123,260 B1 | 9/2021 | Arceneaux | |
| 2004/0171911 A1 | 9/2004 | Zurita | |
| 2008/0146870 A1* | 6/2008 | Marchello | A61F 5/41 600/38 |
| 2015/0164678 A1 | 6/2015 | Lee | |

(Continued)

*Primary Examiner* — Samuel G Gilbert
(74) *Attorney, Agent, or Firm* — Marshall & Melhorn, LLC

(57) ABSTRACT

A therapeutic device and a method of making a therapeutic device. The therapeutic device has a body portion having a first end, a second end, a first end portion, a second end portion, and an intermediate portion interposed between the first and second end portions. Extending inward into at least a portion of the body portion of the therapeutic device from at least a portion of the first end of the therapeutic device is a receiving portion. At least a portion of a surface defining the receiving portion has a shape needed to apply a suction force onto another object needed to secure at least a portion of the object within the receiving portion of the therapeutic device.

14 Claims, 8 Drawing Sheets

(56) References Cited

U.S. PATENT DOCUMENTS

| | | | |
|---|---|---|---|
| 2016/0008218 A1* | 1/2016 | Murison | A61H 19/40 601/46 |
| 2016/0151226 A1* | 6/2016 | Leddy | A61F 5/41 600/38 |
| 2020/0146870 A1* | 5/2020 | Castaneda | A61F 5/41 |

* cited by examiner

THERAPEUTIC DEVICE FOR ALLEVIATING A SEXUAL DYSFUNCTION AND METHOD OF MAKING THE SAME

CROSS-REFERENCE TO RELATED APPLICATION

This application is entitled to claim the benefit of, and claims priority to, U.S. provisional patent application Ser. No. 63/086,108 filed Oct. 1, 2020, the entire disclosure of which is incorporated herein by reference.

FIELD OF THE DISCLOSURE

The present disclosure relates to a therapeutic device that is operable to alleviate or remedy a sexual dysfunction. Additionally, the present disclosure relates to a method of making a therapeutic device that is operable to alleviate or remedy a sexual dysfunction.

BACKGROUND OF THE DISCLOSURE

Various therapeutic devices and methods of alleviating a sexual dysfunction, such as erectile dysfunction (ED) or impotence, are known in the art. One such method of alleviating a sexual dysfunction is to treat it with pharmaceuticals and prescription pills which require the user to attend a doctor's appointment to obtain. Such appointments can be uncomfortable and are undesirable. Once the user has attended the appointment with their doctor and obtained the necessary prescription, the medication itself is very expensive and may not be covered by the user's insurance. Even if the user does all this, they have to worry about whether or not they will suffer from one or more side effects such as blurred vision, nausea, dizziness, muscle pain, headaches, and priapism to name a few.

Other such methods for alleviating a sexual dysfunction, such as erectile dysfunction (ED) or impotence, is to treat it with a medical device that is worn on an intromittent organ of a male organism. Such devices are painful for the user to wear, are uncomfortable for the user to wear, and typically result in an erection that is uncomfortable and unnatural feeling to the user. For example, such devices require the use of a belt or strap that is wrapped around the user's waist or midsection and/or require the use of a loop or attachment that wraps around the user's reproductive glands or testicles.

As a result, it would therefore be advantageous to develop a therapeutic device that is capable of alleviating a sexual dysfunction that is securable to the user in a comfortable manner without the use of any belts or straps that are wrapped around the user's waist or midsection and/or loops or attachments that wrap around the user's reproductive glands or testicles and further do not require the use of prescription medications.

SUMMARY OF THE DISCLOSURE

In concordance and agreement with the present disclosure, a therapeutic device and a method of making a therapeutic device, has surprisingly been discovered. The therapeutic device has a body portion having a first end, a second end, a first end portion, a second end portion, and an intermediate portion interposed between the first and second end portions. Extending inward into at least a portion of the body portion of the therapeutic device from at least a portion of the first end of the therapeutic device is a receiving portion. At least a portion of a surface defining the receiving portion has a shape needed to apply a suction force onto another object needed to secure at least a portion of the object within the receiving portion of the therapeutic device.

In one embodiment, a therapeutic device, comprises: a first body portion having a first end, a second end, a first end portion, a second end portion, and an intermediate portion interposed between the first and second end portions; and a receiving portion may extend inward into the first body portion from at least a portion of the first end, wherein at least a portion of an inner surface of the receiving portion is configured to provide at least a partial vacuum between the at least a portion of the inner surface of the receiving portion and at least a portion of an object at least partially disposed within the receiving portion of the therapeutic device.

As aspects of certain embodiments, the first body portion is formed from at least one of a polymeric composition, an elastomeric composition, a silicone composition, a siloxane composition, a poly-siloxane composition, and a biomimetic composition.

As aspects of certain embodiments, an outer surface of the first body portion may include one or more enhancement portions.

As aspects of certain embodiments, a thickness of the first body portion between the inner surface of the receiving portion and an outer surface of the first body portion is substantially constant across a length of the therapeutic device.

As aspects of certain embodiments, a thickness of the first body portion between the inner surface of the receiving portion and an outer surface of the first body portion is variable across a length of the therapeutic device.

As aspects of certain embodiments, the inner surface of the receiving portion extends at an angle relative to a centerline of the therapeutic device.

As aspects of certain embodiments, the angle of the inner surface is less than 45°.

As aspects of certain embodiments, the second end portion is configured to receive at least a portion of a fluid discharged from the object.

As aspects of certain embodiments, at least a portion of the first body portion includes at least one coating.

As aspects of certain embodiments, the at least one coating is a friction reducing coating.

As aspects of certain embodiments, the at least one coating is at least one of formed on an outer surface of and impregnated into the at least a portion of the first body portion.

As aspects of certain embodiments, the therapeutic device further comprising a second body portion disposed in the receiving portion.

As aspects of certain embodiments, the second body portion is formed from at least one of a polymeric composition, an elastomeric composition, a silicone composition, a siloxane composition, a poly-siloxane composition, and a biomimetic composition.

As aspects of certain embodiments, the second body portion extends at an angle relative to a centerline of the therapeutic device.

As aspects of certain embodiments, the angle of the second body portion is less than 45°.

As aspects of certain embodiments, at least a portion of e first end portion includes at least one third portion.

As aspects of certain embodiments, a distance between a centerline of the therapeutic device and an inner surface of the at least one third portion is less than a distance from e centerline of the therapeutic device and the inner surface of the receiving portion.

In another embodiment, a therapeutic device, comprises: a first body portion having a first end, a second end, a first end portion, a second end portion, and an intermediate portion interposed between the first and second end portions; and a receiving portion may extend inward into the first body portion from at least a portion of the first end, wherein at least a portion of an inner surface of the receiving portion is configured to exert an amount of suction force on at least a portion of an object at least partially disposed within the receiving portion of the therapeutic device.

As aspects of certain embodiments, the amount of suction force exerted on the object facilies a flow of a fluid into the object.

In yet another embodiment, a method of forming a therapeutic device, comprises: providing one or more mold members, a first component, a second component, and at least one core member; weighing an amount of the first component and an amount of the second component to produce a pre-determined ratio; mixing the amount of the first component with the amount of the second component to form a mixture thereof; and allowing the mixture of the first component and the second component to cure to form a therapeutic device.

BRIEF DESCRIPTION OF THE DRAWINGS

The above, as well as other advantages of the present disclosure, will become readily apparent to those skilled in the art from the following detailed description when considered in light of the accompanying drawings in which.

DETAILED DESCRIPTION OF THE DISCLOSURE

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions, directions or other physical characteristics relating to the embodiments disclosed are not to be considered as limiting, unless the claims expressly state otherwise.

Figure 1:
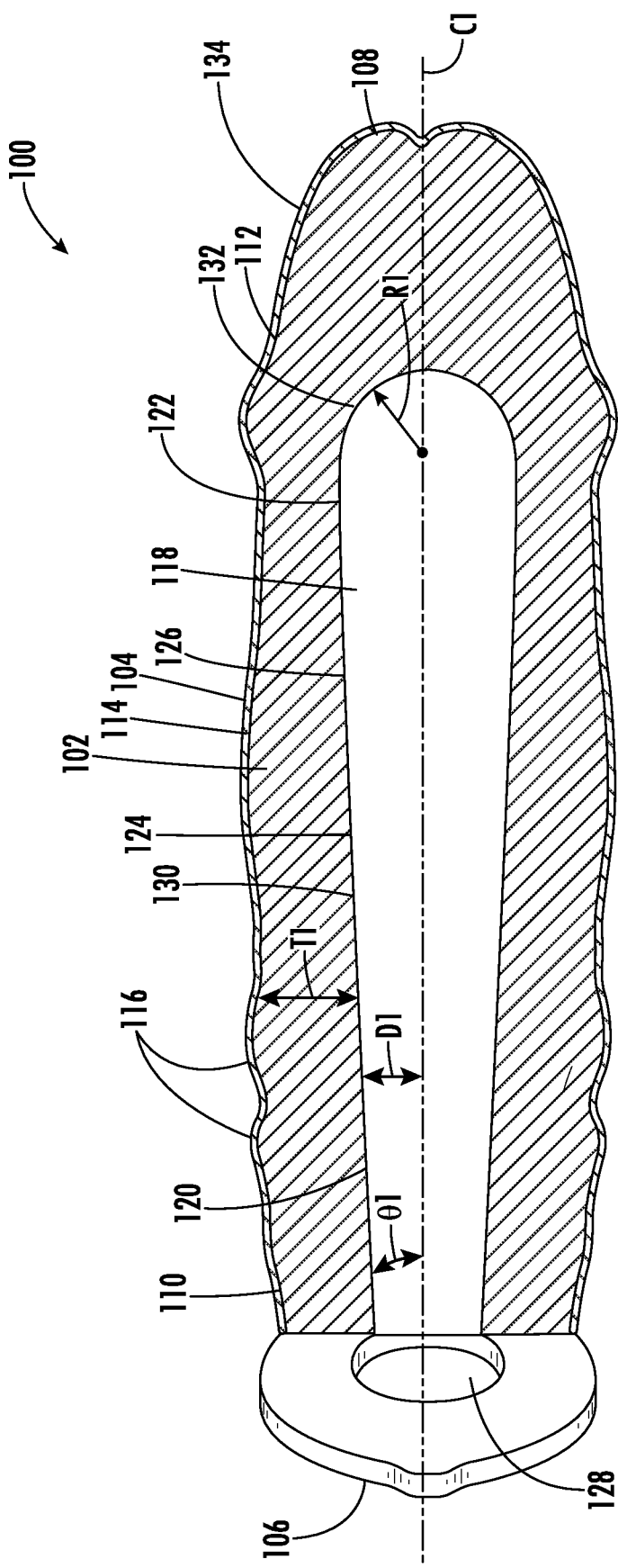
FIG. 1 is a schematic partial cross-sectional side-view of a therapeutic device according to an embodiment of the disclosure.

FIG. 1 provides a schematic partial cross-sectional side-view of a therapeutic device 100 according to an embodiment of the disclosure. The therapeutic device 100 may be utilized by a user (not shown) in order to alleviate a sexual dysfunction. It is within the scope of this disclosure and as a non-limiting example that the sexual dysfunction may be erectile dysfunction (ED) and/or impotence experienced.

As illustrated in FIG. 1 of the disclosure and as a non-limiting example, the therapeutic device 100 may include a first body portion 102 having an outer surface 104, a first end 106, a second end 108, a first end portion 110, a second end portion 112, and an intermediate portion 114 interposed between the first and second end portions 110 and 112 of the therapeutic device 100. At least a portion of the outer surface 104 of the first body portion 102 of the therapeutic device 100 may have a size and shape that is substantially similar to that of an intromittent organ. It is within the scope of this disclosure and as a non-limiting example that the intromittent organ may be a male penis. As a non-limiting example, the first body portion 102 of the therapeutic device 100 may be made of a polymeric composition, an elastomeric composition, a silicone composition, siloxane composition, a poly-siloxane composition, and/or a biomimetic composition.

In accordance with an embodiment of the disclosure and as a non-limiting example, the outer surface 104 of the first body portion 102 of the therapeutic device 100 may include one or more pleasure enhancement portions 116 thereon. The one or more pleasure enhancement portions 116 may aid in enhancing an amount of pleasure received from another user (not shown) during use of the therapeutic device 100. It is within the scope of this disclosure and as a non-limiting example that the one or more pleasure enhancement portions 116 may be one or more raised portions extending outward from the outer surface 104 of the therapeutic device 100 and/or one or more ribs circumferentially extending outward from and around the outer surface 104 of the first body portion 102 of the therapeutic device 100.

A receiving portion 118 may extend inward into the first body portion 102 from at least a portion of the first end 106 of the first body portion 102 of the therapeutic device 100. As illustrated in FIG. 1 and as a non-limiting example, the receiving portion 118 may have a first end portion 120, a second end portion 122, and an intermediate portion 124 interposed between the first and second end portions 120 and 122. The receiving portion 118 may be of a size and shape to receive and/or retain at least a portion of an intromittent organ (not shown) of the user (not shown) therein. As previously discussed, it is within the scope of this disclosure and as a non-limiting example that the intromittent organ (not shown) may be a male penis.

At least a portion of a surface 126 defining the receiving portion 118 within the therapeutic device 100 may have a shape such that a partial vacuum is created between the surface 126 of the receiving portion 118 of the therapeutic device 100 and the intromittent organ (not shown) of the user (not shown). The partial vacuum produces one or more areas of lowered (or reduced) pressure within the receiving portion 118 that aids in creating (or producing) an amount of adhesion between the intromittent organ (not shown) of the user (not shown) and the surface 126 of the receiving portion 118 of the therapeutic device 100. It is therefore to be understood that the surface 126 defining the receiving portion 118 aids in creating an amount of suction force between the surface 126 and the intromittent organ (not shown) of the user (not shown) that aids in securing at least a portion of the therapeutic device 100 to at least a portion of the intromittent organ (not shown) of the user (not shown). This suction force exerted onto the user's intromittent organ (not shown) aids in stretching intromittent organ (not shown) outward which aids in encouraging and promoting the flow of an amount of blood into the intromittent organ (not shown) needed to obtain and/or maintain an erection. As a result, the therapeutic device 100 aids in alleviating a sexual dysfunction such as but not limited to ED and/or impotence in a natural a non-pharmaceutical manner.

The therapeutic device 100 may have a thickness T1 that is measured from the surface 126 defining the receiving portion 118 to the outer surface 104 of the first body portion 102 of the therapeutic device 100. The thickness T1 of the therapeutic device 100 may be such that the therapeutic device 100 may provide the support needed for a flaccid intromittent organ (not shown) to engage in sexual relations. As a result, the therapeutic device 100 allows the user (not shown) to engage in sexual relations even if the intromittent organ (not shown) of the user (not shown) is unable to obtain and maintain an erection. It is within the scope of this disclosure and as a non-limiting example that the thickness T1 may be substantially constant across the length of the therapeutic device 100 and/or may have a variable thickness the length of the therapeutic device 100.

As best seen in FIG. 1 of the disclosure and as a non-limiting example, the receiving portion 118 may include an opening 128 in the first end 106 of the first body portion 102 of the therapeutic device 100. The opening 128 of the receiving portion 118 may be of a size and shape to receive and/or retain at least a portion of the intromittent organ (not shown) of the user (not shown) therein. Additionally, the opening 128 provides the user (not shown) with access to the receiving portion 118 within the first body portion 102 of the therapeutic device 100. It is within the scope of this disclosure and as a non-limiting example that the opening 128 may have a substantially circular cross-sectional shape, a substantially oval cross-sectional shape, a substantially elliptical cross-sectional shape, or any other shape that is substantially similar to the cross-sectional shape of an outer surface of an intromittent organ (not shown).

At least a portion of the first end portion 120 and/or at least a portion of the intermediate portion 124 of the surface 126 defining the receiving portion 118 may include one or more first portions 130. In accordance with the embodiment illustrated in FIG. 1 and as a non-limiting example, the surface 126 defining the receiving portion 118 at the one or more first portions 130 may extend at an angle θ1 relative to a centerline C1 extending lengthwise through the therapeutic device 100. In certain embodiments, the angle θ1 is less than 45° relative to the centerline C1. In other embodiments, the angle θ1 is less than 30° relative to the centerline C1. In yet other embodiments, the angle θ1 is less than 15° relative to the centerline C1 and more preferably less than 5°. As a result, a distance D1 between the centerline C1 and the surface 126 defining the receiving portion 118 may increase along the centerline C1 as the one or more first portions 130 extend from the first end portion 120 toward the second end portion 122 of the receiving portion 118. The one or more first portions 130 aid in creating the suction force that is exerted onto the intromittent organ (not shown) of the user (not shown) needed to secure the therapeutic device 100 to the user's intromittent organ (not shown), aid in promoting the flow of blood into the intromittent organ (not shown), and/or aid in helping the user lot shown) obtain and/or maintain an erection. It is within the scope of this disclosure and as a non-limiting example that the one or more first portions 130 may have a substantially frustum cross-sectional shape and/or a substantially frusto-conical cross-sectional shape.

At least a portion of the second end portion 122 of the receiving portion 118 of the therapeutic device 100 may include one or more second portions 132. The one or more second portions 132 may be of a size and shape to receive and/or retain at least a portion of a head (not shown) of the user's intromittent organ (not shown). Additionally, the one or more second portions 132 of the receiving portion 118 may have a size and shape needed to receive and/or retain an amount of ejaculate and/or semen therein. The one or more second portions 132 may aid in creating the suction force that is exerted onto the intromittent organ (not shown) of the user (not shown) needed to secure the therapeutic device 100 to the user's intromittent organ (not shown), aid in promoting the flow of blood into the intromittent organ (not shown), and/or aid in helping the user (not shown) obtain and/or maintain an erection.

As illustrated in FIG. 1 and as a non-limiting example, at least a portion of the one or more second portions 132 may have a shape that is defined by a radius R1 extending from the centerline C1. It is within the scope of this disclosure and as a non-limiting example that the one or more second portions 132 may have a substantially arcuate cross-sectional shape, a substantially heir hemisphere cross-sectional shape, and/or a substantially dome like cross-sectional shape.

It is therefore within the scope of this disclosure and as a non-limiting example that the receiving portion 118 of the therapeutic device 100 may have a substantially elongated tear drop shape with a truncated end.

In accordance with the embodiment illustrated in FIG. 1 and as a non-limiting example, the first body portion 102 of the therapeutic device 100 may include one or more coatings 134 thereon. The one or more costings 134 may cover at least a portion of the outer surface 104 of the first body portion 102 of the therapeutic device 100. The one or more coatings 134 may be a friction reducing coating that aids in reducing the overall coefficient of friction between the first body portion 102 of the therapeutic device 100 and another surface (not shown). It is within the scope of this disclosure and as a non-limiting example that the one or more coatings 134 may be a lubricant composition, an oil composition, and/or any other composition that aids in reducing the overall amount of friction between the first body portion 102 of therapeutic device 100 and another surface (not shown). As a non-limiting example, the oil composition may be a Durian Tree Nut Oil.

According to an embodiment of the disclosure and as a non-limiting example, the one or more coatings 134 may be impregnated or incorporated within the first body portion 102 of the therapeutic device 100. It is therefore to be understood that the composition of the one or more coatings 134 may be incorporated into the composition of the first body portion 102 of the therapeutic device 100. This aids in forming a therapeutic device 100 having one or more coatings 134 that are self-repairing. As a result, the one or more coatings 134 do not need to be applied to the first body portion 102 of the therapeutic device 100 multiple times thereby providing a therapeutic device 100 that is more user friendly.

According to an embodiment of the disclosure and as a non-limiting example, the surface 126 defining the receiving portion 118 within the therapeutic device 100 may not include the one or more coatings 134. By providing a therapeutic device 100 having a receiving portion 118 without one or more coatings 134 thereon may aid in securing the at least a portion of the first body portion 102 of the therapeutic device 100 to at least a portion of the user's intromittent organ (not shown) in a comfortable and secure manner.

As a result, the therapeutic device 100 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 2:
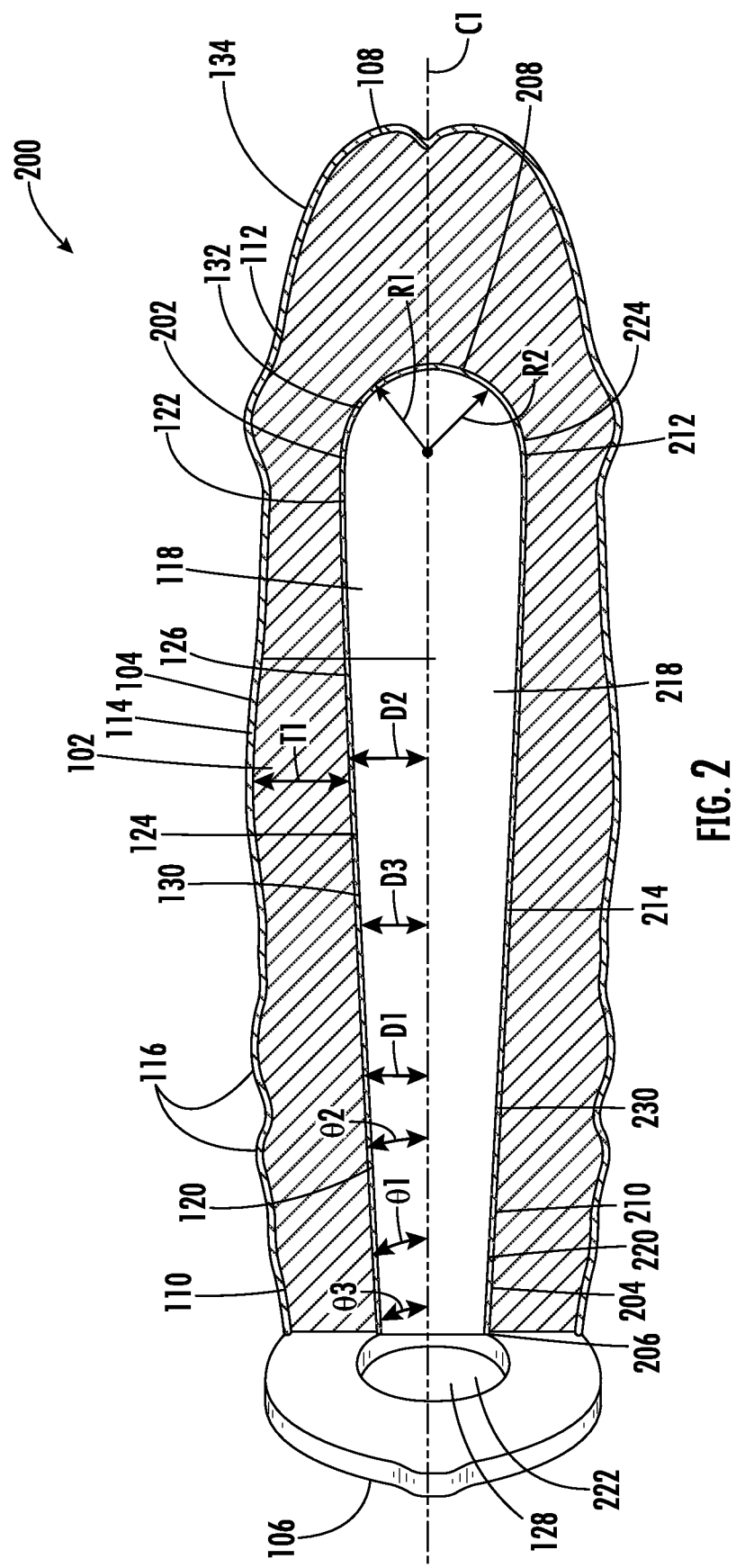
FIG. 2 is a schematic partial cross-sectional side-view of a therapeutic device according to an alternative embodiment of the disclosure.

FIG. 2 provides a schematic partial cross-sectional sideview of a therapeutic device 200 according to an alternative embodiment of the disclosure. The therapeutic device 200 illustrated in FIG. 2 is the same as the therapeutic device 100 illustrated in FIG. 1, except where specifically noted below. As illustrated in FIG. 2 of the disclosure and as a non-limiting example, the therapeutic device 200 may include a second body portion 202 that is received and/or retained within at least a portion of the receiving portion 118 of the first body portion 102 of the therapeutic device 200.

In accordance with the embodiment illustrated in FIG. 2 and as a non-limiting example, the second body portion 202 may have an outer surface 204, a first end 206, a second end 208, a first end portion 210, a second end portion 212, and an intermediate portion 214 interposed between the first and second end portions 210 and 212. At least a portion of the outer surface 204 of the second body portion 202 may be in direct contact with at least a portion of the surface 126 defining the receiving portion 118 of the first body portion 102 within the therapeutic device 200. It is therefore within the scope of this disclosure and as a non-limiting example that the outer surface 204 of the second body portion 202 may have a shape that is complementary to the shape of the surface 126 defining the receiving portion 118 of the first body portion 102 of the therapeutic device 200. As a non-limiting example, the second body portion 202 of the therapeutic device 200 may be made of a polymeric composition, an elastomeric composition, a silicone composition, siloxane composition, a poly-siloxane composition, and/or a biomimetic composition.

According to an embodiment of disclosure and as a non-limiting example, the second body portion 202 may be made of the same material as the first body portion 102 without the coating material 134 included therein. This aids in ensuring that the first body portion 102 includes the one or more coatings 134 thereon while providing a second body portion 202 that does not include the one or more coatings 134 thereon. As previously discussed, by providing a therapeutic device 200 that does not include one or more coatings 134 between the therapeutic device 200 and the user's intromittent organ (not shown) it aids in increasing the suction force exerted onto the user's intromittent organ (not shown) by the therapeutic device 200, it aids in promoting the flow of blood into the user's intromittent organ (not shown), and/or aids in promoting the user's (not shown) ability to obtain and/or maintain an erection.

As illustrated in FIG. 2 and as a non-limiting example, the outer surface 204 of the second body portion 202 may extend at an angle $\theta_2$ relative to the centerline C1 extending lengthwise through the therapeutic device 200. In certain embodiments, the angle $\theta_2$ is less than 45° relative to the centerline C1. In other embodiments, the angle $\theta_2$ is less than 30° relative to the centerline C1. In yet other embodiments, the angle $\theta_2$ is less than 15° relative to the centerline C1 and more preferably less than 5°. As a result, a distance D2 between the centerline C1 and the outer surface 204 of the second body portion 202 may increase along the centerline C1 as the outer surface 204 extends from the first end portion 210 toward the second end portion 212 of the second body portion 202. This aids in preventing the second body portion 202 from being pulled out of the receiving portion 118 within the first body portion 102 of the therapeutic device 200. It is within the scope of this disclosure and as a non-limiting example that the angle $\theta_2$ may be substantially equal to the angle $\theta_1$ and/or the distance D2 may be substantially equal to the distance D1.

Additionally, it is within the scope of this disclosure and as a non-limiting example that the angle $\theta_2$ may be greater than the angle $\theta_1$ and/or the distance D2 may be greater than the distance D1. By providing the second body portion 202 of the therapeutic device 200 with an angle $\theta_2$ that is greater than the angle $\theta_1$ and/or a distance D2 that is greater than the distance D1 it aids in increasing the overall amount of force exerted onto the second body portion 202 by the first body portion 102 when inserted into the receiving portion 118 of the first body portion 102. This aids in preventing the second body portion 202 from inadvertently and unintentionally being removed from the receiving portion 118 of the body portion 202.

According to the embodiment illustrated in FIG. 2 and as a non-limiting example, at least a portion of the outer surface 204 of the second body portion 202 may be adhered and/or bonded to at least a portion of surface 126 defining the receiving portion 118 of the first body portion 102 within the therapeutic device 200. It is within the scope of this disclosure and as a non-limiting example, that the bond created between the first and second body portions 102 and 202 may be created by using one or more adhesives and/or one or more welds. As a non-limiting example, the one or more welds may be created by using one or more friction welds, one or more energy beam welds, one or more laser welds, one or more electron beam welds, and/or one or more x-ray welds.

The second body portion 202 of the therapeutic device 200 may include an additional receiving portion 218 therein. The additional receiving portion 218 may be of a size and shape to receive and/or retain at least a portion of the user's intromittent organ (not shown) therein.

At least a portion of a surface 220 defining the additional receiving portion 218 within the second body portion 202 of the therapeutic device 200 may have a shape such that a partial vacuum is created between the surface 220 of the additional receiving portion 218 of the therapeutic device 200 and the user's intromittent organ (not shown). The partial vacuum produces one or more areas of lowered (or reduced) pressure within the additional receiving portion 218 that aids in creating (or producing) an amount of adhesion between the user's intromittent organ (not shown) and the surface 218 of the additional receiving portion 218 of the therapeutic device 200. It is therefore to be understood that the surface 220 defining the receiving portion 218 aids in creating an amount of suction force between the surface 218 and the user's intromittent organ (not shown) that aids in securing at least a portion of the therapeutic device 200 to at least a portion of the user's intromittent organ (not shown). This suction force exerted onto the user's intromittent organ (not shown) aids in stretching intromittent organ (not shown) outward which aids in encouraging and promoting the flow of an amount of blood into the intromittent organ (not shown) needed to obtain and/or maintain an erection. As a result, the therapeutic device 200 aids in alleviating a sexual dysfunction such as but not limited to ED and/or impotence in a natural a non-pharmaceutical manner.

As best seen in FIG. 2 of the disclosure and as a non-limiting example, the additional receiving portion 218 may include an opening 222 in the first end 206 of the second body portion 202 of the therapeutic device 200. The opening 222 of the additional receiving portion 218 may be of a size and shape to receive and/or retain at least a portion of the user's intromittent organ (not shown) therein. Additionally, the opening 222 may provide the user (not shown) with access to the receiving portion 118 and the additional receiving portion 218 within the first and second body portions 102 and 202 of the therapeutic device 200. As a non-limiting example, the opening 222 may have a substantially circular cross-sectional shape, a substantially oval cross-sectional shape, a substantially elliptical cross-sectional shape, or any other shape that is substantially similar to the cross-sectional shape of an outer surface of an intromittent organ (not shown).

It is within the scope of this disclosure and as a non-limiting example that at least a portion of the opening 128 of the receiving portion 118 within the first body portion 102 may be elastically deformed outward thereby allowing at least a portion of the second body portion 202 to be received and/or retained within at least a portion of the receiving portion 118.

At least a portion of the first end portion 210 and/or at least a portion of the intermediate portion 214 of the surface 220 defining the additional receiving portion 218 may include one or more first portions 230. In accordance with the embodiment illustrated in FIG. 2 and as a non-limiting example, the surface 220 defining the additional receiving portion 218 at the one or more first portions 230 may extend at an angle θ3 relative to the centerline C1 extending lengthwise through the therapeutic device 200. In certain embodiments, the angle θ3 is less than 45° relative to the centerline C1. In other embodiments, the angle θ3 is less than 30° relative to the centerline C1. In yet other embodiments, the angle θ3 is less than 15° relative to the centerline C1, and more preferably less than 5°. Additionally, it is within the scope of this disclosure and as a non-limiting example that the angle θ3 may be less than at least one of the angle θ1 and the angle θ2. As a result, a distance D3 between the centerline C1 and the surface 220 defining the additional receiving portion 218 may increase along the centerline C1 as the one or more first portions 230 extend from the first end portion 210 toward the second end portion 212 of the additional receiving portion 218. The one or more first portions 230 aid in creating the suction force that is exerted onto the user's intromittent organ (not shown) needed to secure the therapeutic device 200 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more first portions 230 may have a substantially frustum cross-sectional shape and/or a substantially frusto-conical cross-sectional shape.

At least a portion of the second end portion 212 of the additional receiving portion 218 of the therapeutic device 200 may include one or more second portions 224. The one or more second portions 224 may be of a size and shape to receive and/or retain at least a portion of a head (not shown) of the user's intromittent organ (not shown). Additionally, the one or more second portions 224 of the additional receiving portion 218 may have a size and shape needed to receive and/or retain an amount of ejaculate and/or semen therein. The one or more second portions 224 may aid in creating the suction force that is exerted onto the user's intromittent organ (not shown) needed to secure the therapeutic device 200 to the user's intromittent organ (not shown), aid in promoting the flow of blood into the intromittent organ (not shown), and/or aid in helping the user (not shown) obtain and/or maintain an erection.

As illustrated in FIG. 2 and as a non-limiting example, at least a portion of the one or more second portions 224 may have a shape that is defined by a radius R2 extending from the centerline C1. It is within the scope of this disclosure and as a non-limiting example that the one or more second portions 224 may have a substantially arcuate cross-sectional shape, a substantially hemisphere cross-sectional shape, and/or a substantially dome like cross-sectional shape. As a non-limiting example, the radius R2 may be less than the radius R1.

It is therefore within the scope of this disclosure and as a non-limiting example that the additional receiving portion 218 of the therapeutic device 200 may have a substantially elongated tear drop shape with a truncated end.

By providing the therapeutic device 200 with a second body portion 202, it aids in ensuring that the one or more coatings 134 do not form between the therapeutic device 200 and the intromittent organ (not shown) of the user (not shown). As a result, the therapeutic device 200 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 3:
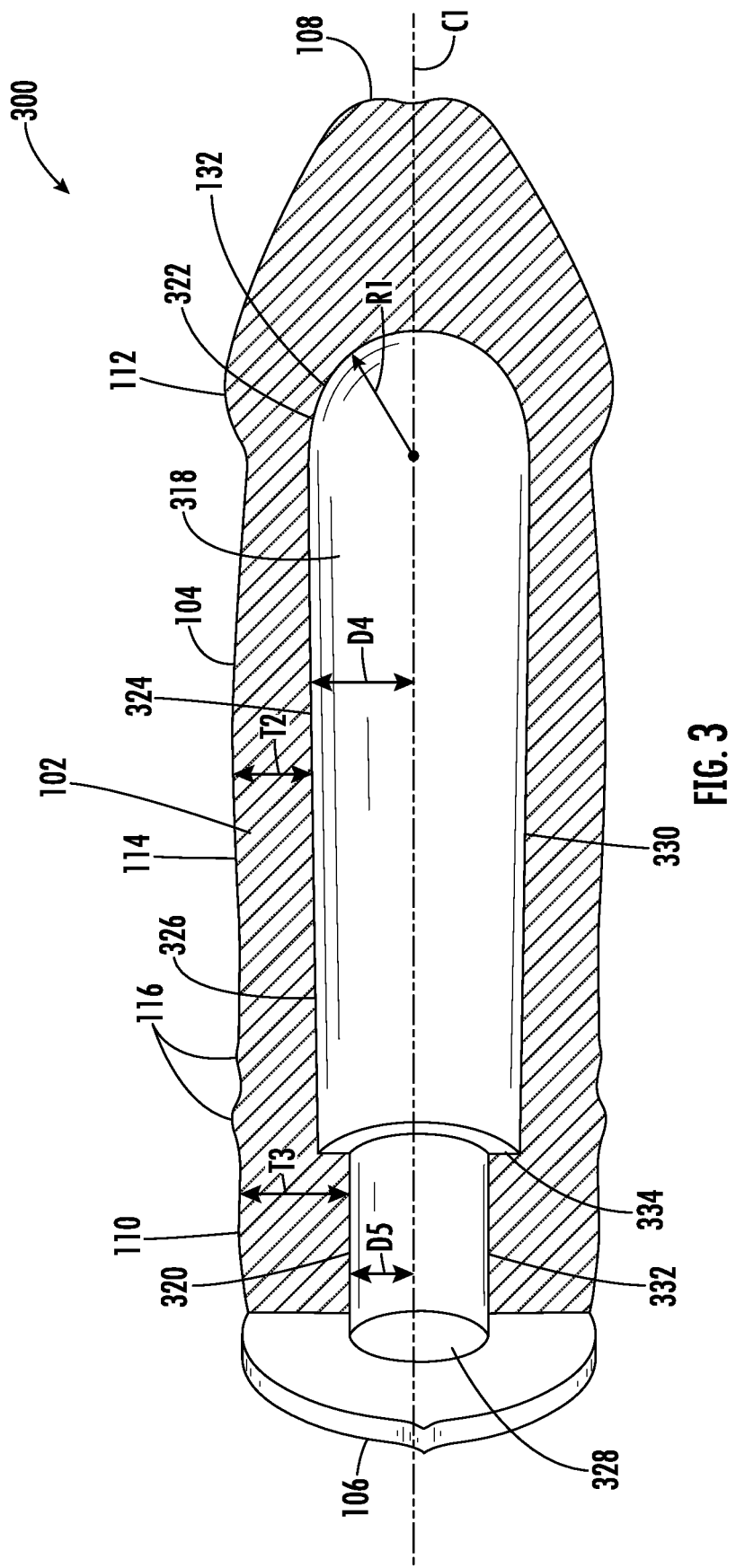
FIG. 3 is a schematic partial cross-sectional side-view of a therapeutic device according to yet another embodiment of the disclosure.

FIG. 3 provides a schematic partial cross-sectional side-view of a therapeutic device 300 according to yet another embodiment of the disclosure. The therapeutic device 300 illustrated in FIG. 3 is the same as the therapeutic devices 100 and 200 illustrated in FIGS. 1 and 2, except where specifically noted below. As illustrated in FIG. 3 of the disclosure and as a non-limiting example, the therapeutic device 300 may include a receiving portion 318 therein.

In accordance with the embodiment illustrated in FIG. 3 and as a non-limiting example, the receiving portion 318 may extend inward into the first body portion 102 from at least a portion of the first end 106 of the first body portion 102 of the therapeutic device 300. As illustrated in FIG. 3 and as a non-limiting example, the receiving portion 318 may have a first end portion 320, a second end portion 322, and an intermediate portion 324 interposed between the first and second end portions 320 and 322. The receiving portion 318 may be of a size and shape to receive and/or retain at least a portion of the user's intromittent organ (not shown) therein.

At least a portion of a surface 326 defining the receiving portion 318 within the therapeutic device 300 may have a shape such that a partial vacuum is created between the surface 326 of the receiving portion 318 of the therapeutic device 300 and the intromittent organ (not shown) of the user (not shown). The partial vacuum produces one or more areas of lowered (or reduced) pressure within the receiving portion 318 that aids in creating (or producing) an amount of adhesion between the user's intromittent organ (not shown) and the surface 326 of the receiving portion 318 of the therapeutic device 300. It is therefore to be understood that the surface 326 defining the receiving portion 318 aids in creating an amount of suction force between the surface 326 and the user's intromittent organ (not shown) that aids in securing at least a portion of the therapeutic device 300 to at least a portion of the user's intromittent organ (not shown). This suction force exerted onto the user's intromittent organ (not shown) aids in stretching intromittent organ (not shown) outward which aids in encouraging and promoting the flow of an amount of blood into the intromittent organ (not shown) needed to obtain and/or maintain an erection. As a result, the therapeutic device 300 aids in alleviating a sexual dysfunction such as but not limited to ED and/or impotence in a natural a non-pharmaceutical manner.

As best seen in FIG. 3 and as a non-limiting example, the receiving portion 318 may include an opening 328 in the first end 106 of the first body portion 102 of the therapeutic device 300. The opening 328 of the receiving portion 318 may be of a size and shape to receive and/or retain at least a portion of the user's intromittent organ (not shown) therein. Additionally, the opening 328 provides the user (not shown) with access to the receiving portion 318 within the first body portion 102 of the therapeutic device 300. It is within the scope of this disclosure and as a non-limiting example that the opening 328 may have a substantially circular cross-sectional shape, a substantially oval cross-sectional shape, a substantially elliptical cross-sectional shape, or any other shape that is substantially similar to the cross-sectional shape of an outer surface of an intromittent organ (not shown).

At least a portion of the intermediate portion 324 of the surface 326 defining the receiving portion 318 may include one or more first portions 330. In accordance with the embodiment illustrated in FIG. 3 and as a non-limiting example, the surface 326 defining the receiving portion 318 at the one or more first portions 330 may extend substantially parallel relative to the centerline C1 extending lengthwise through the therapeutic device 300. The one or more first portions 330 aid in creating the suction force that is exerted onto the intromittent organ (not shown) of the user (not shown) needed to secure the therapeutic device 300 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more first portions 330 may have a substantially cylindrical shape.

At least a portion of the first end portion 320 of the surface 326 defining the receiving portion 318 may include one or more third portions 332. In accordance with the embodiment illustrated in FIG. 3 and as a non-limiting example, the surface 326 defining the receiving portion 318 at the one or more third portions 332 may extend substantially parallel relative to the centerline C1 extending lengthwise through the therapeutic device 300. The one or more third portions 332 aid in creating the suction force that is exerted onto the intromittent organ (not shown) of the user (not shown) needed to secure the therapeutic device 300 to the user's intromittent organ (not shown), aid in promoting the flow of blood into the intromittent organ (not shown), aid in preventing the flow of blood out of the user's intromittent organ (not shown), and/or aid in helping the user (not shown) obtain and/or maintain an erection. It is within the scope of this disclosure and as a non-limiting example that the one or more third portions 332 may have a substantially cylindrical shape.

The surface 326 defining the receiving portion 318 in the one or more third portions 332 may be disposed a distance D5 from the centerline C1 of the therapeutic device 300. As illustrated in FIG. 3 and as a non-limiting example, the distance D5 may be less than a distance D4 extending from the centerline C1 to the surface 326 defining the receiving portion 318 in the one or more first portions 330 of the therapeutic device 300.

In accordance with an alternative embodiment of the disclosure and as a non-limiting example, the surface 326 defining the receiving portion 318 may include a transition portion 334. The transition portion 334 may connect at least a portion of an end of the one or more first portions 330, opposite the one or more second portions 132, to at least a portion of the one or more third portions 332. The transition portion 334 aids in creating the suction force that is exerted onto the user's intromittent organ (not shown) needed to secure the therapeutic device 300 to the user's intromittent organ (not shown), aids in promoting the flow of blood into the intromittent organ (not shown), and/or aids in helping the user (not shown) obtain and/or maintain an erection. The transition portion 334 may extend outward from the one or more first portions 330 at an angle relative to the centerline C1. As a non-limiting example, the transition portion 334 may extend substantially perpendicular relative to the centerline C1 extending through the therapeutic device 300.

The therapeutic device 300 may have a thickness T2 that is measured from the surface 326 defining the one or more first portions 330 of the receiving portion 318 to the outer surface 104 of the first body portion 102 of the therapeutic device 300. The thickness T2 of the therapeutic device 300 may be such that the therapeutic device 300 may provide the support needed for a flaccid intromittent organ (not shown) to engage in sexual relations. As a result, the therapeutic device 300 allows the user (not shown) to engage in sexual relations even if the intromittent organ (not shown) of the user (not shown) is unable to obtain and maintain an erection. It is within the scope of this disclosure and as a non-limiting example that the thickness T2 may be substantially constant across the length of the therapeutic device 300 and/or may have a variable thickness the length of the therapeutic device 300.

Additionally, the therapeutic device 300 may have a thickness T3 that is measured from the surface 326 defining the one or more third portions 332 of receiving portion 318 to the outer surface 104 of the first body portion 102 of the therapeutic device 300. It is within the scope of this disclosure and as a non-limiting example that the thickness T3 may be substantially constant across the length of the therapeutic device 300 and/or may have a variable thickness the length of the therapeutic device 300. Additionally, it is within the scope of this disclosure and as a non-limiting example that the thickness T3 may be greater than the thickness T2.

As a result, the therapeutic device 300 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 4:
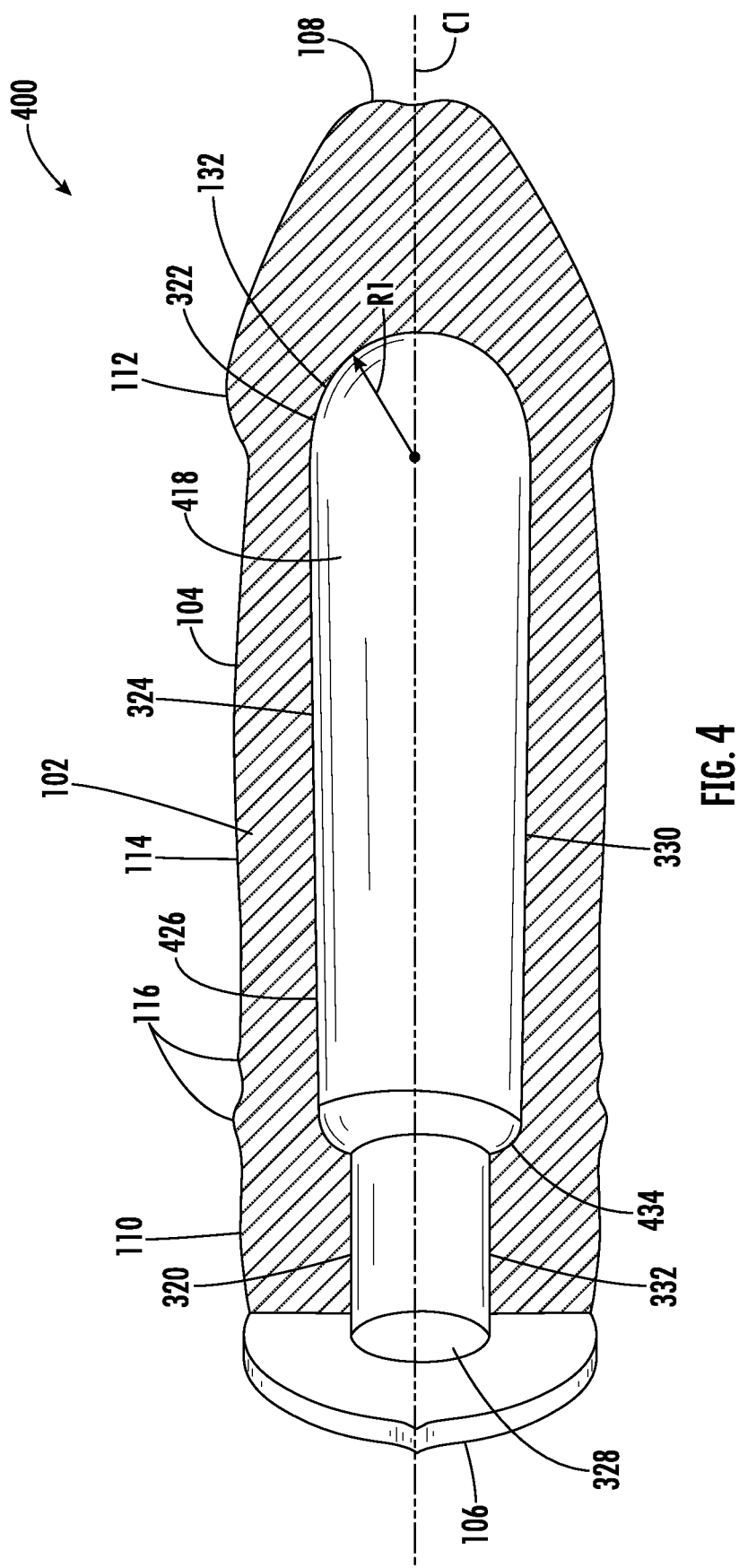
FIG. 4 is a schematic partial cross-sectional side-view of a therapeutic device according to still yet another embodiment of the disclosure.

FIG. 4 provides a schematic partial cross-sectional side-view of a therapeutic device 400 according to still yet another embodiment of the disclosure. The therapeutic device 400 illustrated in FIG. 4 is the same as the therapeutic devices 100, 200, and 300 illustrated in FIGS. 1-3, except where specifically noted below. As illustrated in FIG. 4 of the disclosure and as a non-limiting example, the therapeutic device 400 may include a receiving portion 418 therein.

In accordance with the embodiment illustrated in FIG. 4 and as a non-limiting example, a surface 426 defining the receiving portion 418 may include a transition portion 434. The transition portion 434 may connect at least a portion of an end of the one or more first portions 330, opposite the one or more second portions 132, to at least a portion of the one or more third portions 332 of the receiving portion 418. The transition portion 434 aids in creating the suction force that is exerted onto the user's intromittent organ (not shown) needed to secure the therapeutic device 400 to the user's intromittent organ (not shown), aids in promoting the flow of blood into the intromittent organ (not shown), and/or aids in helping the user (not shown) obtain and/or maintain an erection. As a non-limiting example, the transition portion 434 may have a substantially arcuate cross-sectional shape and/or a substantially concave cross-sectional shape.

As a result, the therapeutic device 400 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 5:
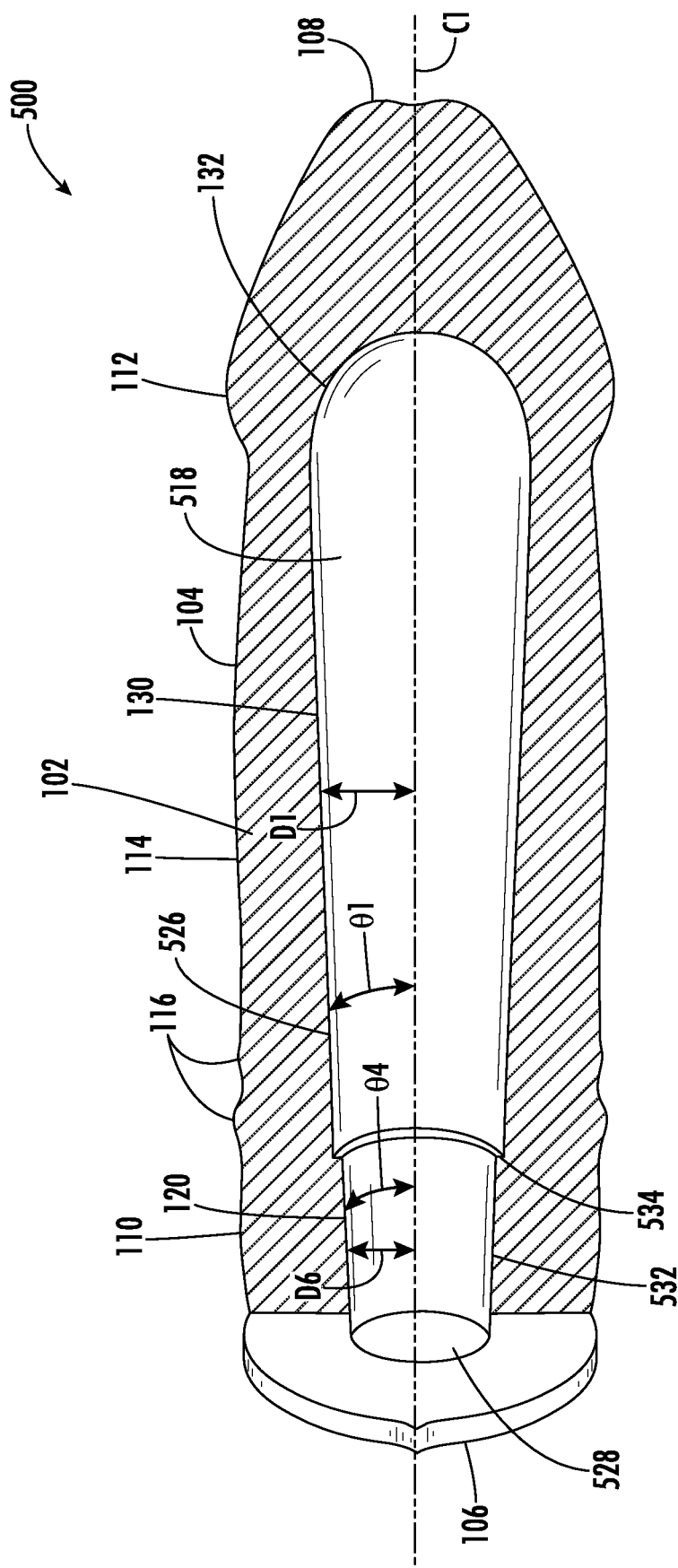
FIG. 5 is a schematic partial cross-sectional side-view of a therapeutic device according to still yet a further embodiment of the disclosure.

FIG. 5 provides a schematic partial cross-sectional side-view of a therapeutic device 500 according to still a further embodiment of the disclosure. The therapeutic device 500 illustrated in FIG. 5 is the same as the therapeutic devices 100, 200, 300, and 400 illustrated in FIGS. 1-4, except where specifically noted below. As illustrated in FIG. 5 of the disclosure and as a non-limiting example, the therapeutic device 500 may include a receiving portion 518 therein.

In accordance with the embodiment illustrated in FIG. 5 and as a non-limiting example at least a portion of a first end portion 120 of the surface 526 defining the receiving portion 518 may include one or more third portions 532. As illustrated in FIG. 5 and as a non-limiting example, the surface 526 defining the receiving portion 518 at the one or more third portions 532 may extend at an angle $\theta 4$ relative to a centerline C1 extending lengthwise through the therapeutic device 500. In certain embodiments, the angle $\theta 4$ is less than 45° relative to the centerline C1. In other embodiments, the angle $\theta 4$ is less than 30° relative to the centerline C1. In yet other embodiments, the angle $\theta 4$ is less than 15° relative to the centerline C1, and more preferably less than 4°. As a result, a distance D6 between the centerline C1 and the surface 526 defining the receiving portion 518 may increase along the centerline C1 as the one or more third portions 532 extend from the first end portion 120 toward the second end portion 122 of the receiving portion 518. The one or more third portions 532 aid in creating the suction force that is exerted onto the intromittent organ (not shown) of the user (not shown) needed to secure the therapeutic device 100 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more first portions 130 may have a substantially frustum cross-sectional shape and/or a substantially frusto-conical cross-sectional shape. As a non-limiting example, the angle $\theta 4$ may be less than at least one of the angle $\theta 1$, the angle $\theta 2$, and the angle $\theta 3$ and/or the distance D6 may be less than the distance D1. Additionally, as another non-limiting example, the angle $\theta 4$ may be greater than at least one of the angle $\theta 1$, the angle $\theta 2$, and the angle $\theta 3$.

As illustrated in FIG. 5 and as a non-limiting example, the surface 526 defining the receiving portion 518 may include the transition portion 534. The transition portion 334 may connect at least a portion of an end of the one or more first portions 130, opposite the one or more second portions 132, to at least a portion of the one or more third portions 532. The transition portion 534 aids in creating the suction force that is exerted onto the user's intromittent organ (not shown) needed to secure the therapeutic device 500 to the user's intromittent organ (not shown), aids in promoting the flow of blood into the intromittent organ (not shown), and/or aids in helping the user (not shown) obtain and/or maintain an erection.

As a result, the therapeutic device 500 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 6:
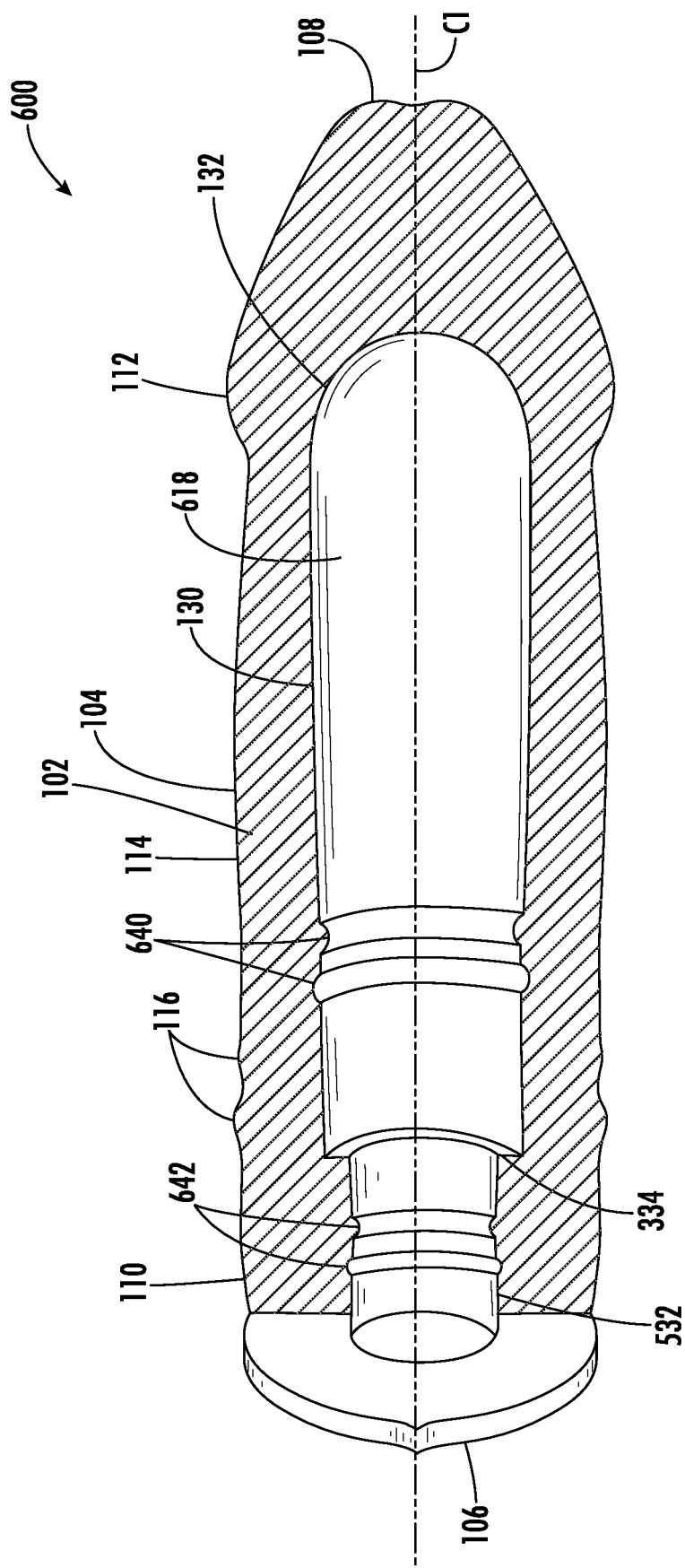
FIG. 6 is a schematic partial cross-sectional side-view of a therapeutic device according to still yet another embodiment of the disclosure.

FIG. 6 provides schematic partial cross-sectional side-view of a therapeutic device 600 according to still yet another embodiment of the disclosure. The therapeutic device 600 illustrated in FIG. 6 is the same as the therapeutic devices 100, 200, 300, 400, and 500 illustrated in FIGS. 1-5, except where specifically noted below. As illustrated in FIG. 6 of the disclosure and as a non-limiting example, the therapeutic device 600 may include a receiving portion 618 therein with one or more first engagement portions 640 and/or one or more second engagement portions 642.

In accordance with the embodiment illustrated in FIG. 6 and as a non-limiting example, the one or more first portions 130 of the receiving portion 618 may include the one or more first engagement portions 640. As illustrated in FIG. 6 of the disclosure and as a non-limiting example, the one or more first engagement portions 640 may circumferentially or helically extend along at least a portion of the one or more first portions 130 of the receiving portion 618 within the therapeutic device 600. The one or more first engagement portions 640 may engage and come in direct contact with at least a portion of the user's intromittent organ (not shown). Additionally, the one or more first engagement portions 640 may aid in creating the suction force that is exerted onto the user's intromittent organ (not shown) needed to secure the therapeutic device 600 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more first engagement portions 640 may extend outward away from the centerline C1 and/or inward toward the centerline C1 of the therapeutic device 600.

According to the embodiment illustrated in FIG. 6 of the disclosure and as a non-limiting example, the one or more third portions 332 of the receiving portion 618 may include the one or more second engagement portions 642. As illustrated in FIG. 6 and as a non-limiting example, the one or more second engagement portions 642 may circumferentially extend along at least a portion of the one or more third portions 332 of the receiving portion 618. The one or more second engagement portions 642 may engage and come in direct contact with at least a portion of the user's intromittent organ (not shown). Additionally, the one or more second engagement portions 642 may aid in creating the suction force that is exerted onto the user's intromittent organ (not shown) needed to secure the therapeutic device 600 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more second engagement portions 642 may extend outward away from the centerline C1 and/or inward toward the centerline C1 of the therapeutic device 600.

As a result, the therapeutic device 600 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 7:
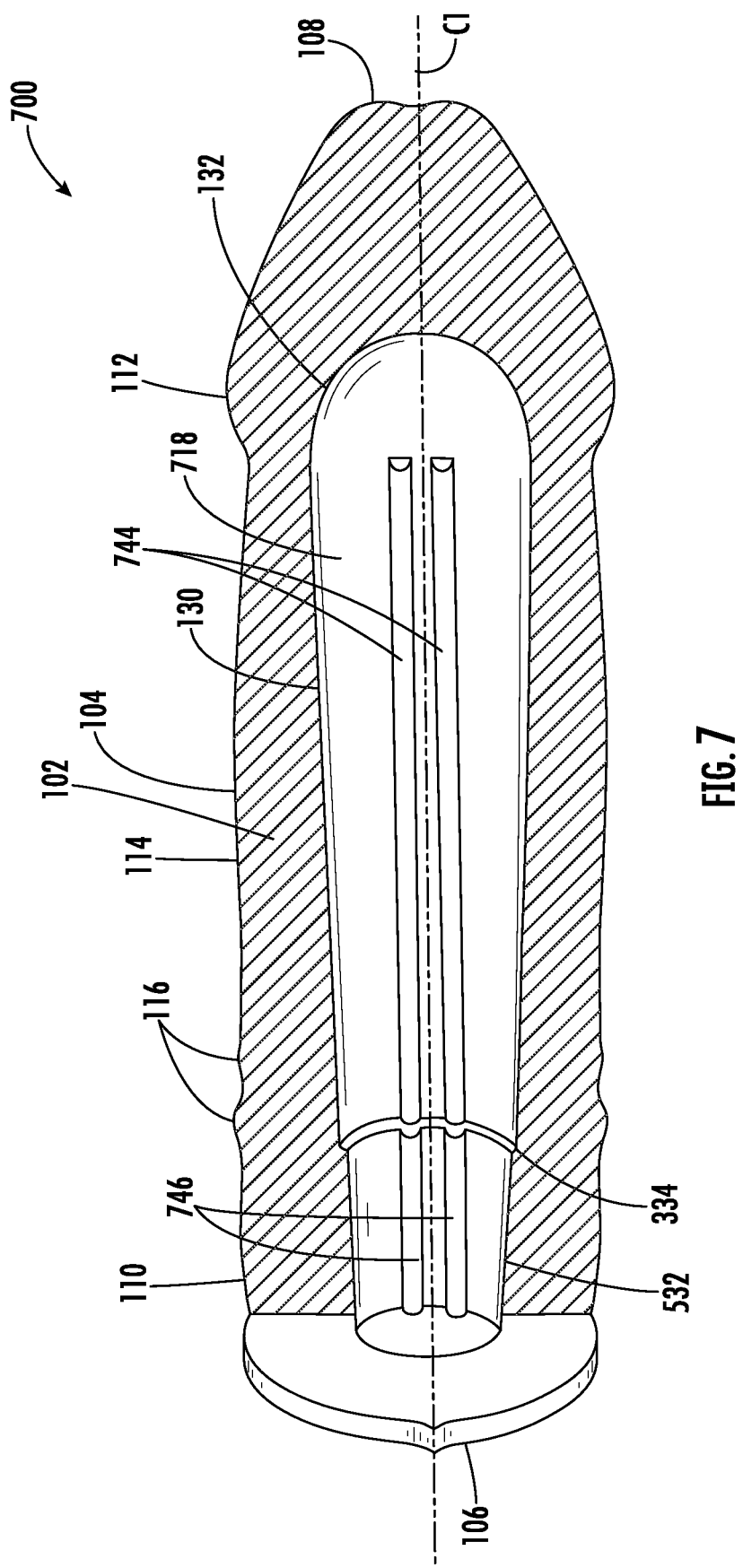
FIG. 7 is a schematic partial cross-sectional side-view of a therapeutic device according to still yet another embodiment of the disclosure.

FIG. 7 provides schematic partial cross-sectional sideview of a therapeutic device 700 according to still yet another embodiment of the disclosure. The therapeutic device 700 illustrated in FIG. 7 is the same as the therapeutic devices 100, 200, 300, 400, 500, and 600 illustrated in FIGS. 1-6, except where specifically noted below. As illustrated in FIG. 7 of the disclosure and as a non-limiting example, the therapeutic device 700 may include a receiving portion 718 therein with one or more third engagement portions 744 and/or one or more fourth engagement portions 746.

In accordance with the embodiment illustrated in FIG. 7 and as a non-limiting example, the one or more first portions 130 of the receiving portion 718 may include the one or more third engagement portions 744. As illustrated in FIG. 7 of the disclosure and as a non-limiting example, at least a portion of the one or more third engagement portions 744 may extend in a substantially linear manner along the length of the one or more first portions 130 of the therapeutic device 700. The one or more third engagement portions 744 may engage and come in direct contact with at least a portion of the user's intromittent organ (not shown). Additionally, the one or more third engagement portions 744 may provide pressure to the deep dorsal vein of the user's intromittent organ (not shown) thereby mimicking the pressure that occurs during a natural erection and promoting the user's (not shown) ability to obtain and/or maintain an erection. Furthermore, the one or more third engagement portions 744 may aid in creating the suction force that is exerted onto the user's intromittent, organ (not shown) needed to secure the therapeutic device 700 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more third engagement portions 744 may extend outward away from the centerline C1 and/or inward toward the centerline C1 of the therapeutic device 700.

According to the embodiment illustrated in FIG. 7 and as a non-limiting example, the one or more third portions 532 of the receiving portion 718 may include the one or more fourth engagement portions 746. As illustrated in FIG. 7 of the disclosure and as a non-limiting example, at least a portion of the one or more fourth engagement portions 746 may extend in a substantially linear manner along the length of the one or more third portions 532 of the therapeutic device 700. The one or more fourth engagement portions 746 may engage and come in direct contact with at least a portion of the user's intromittent organ (not shown). Additionally, the one or more fourth engagement portions 746 may provide pressure to the deep dorsal vein of the user's intromittent organ (not shown) thereby mimicking the pressure that occurs during a natural erection and promoting the user's (not shown) ability to obtain and/or maintain an erection. Furthermore, the one or more fourth engagement portions 746 may aid in creating the suction force that is exerted onto the user's intromittent organ (not shown) needed to secure the therapeutic device 700 to the user's intromittent organ (not shown), aid in promoting the flow of blood into the intromittent organ (not shown), and/or aid in helping the user (not shown) obtain and/or maintain an erection. It is within the scope of this disclosure and as a non-limiting example that the one or more fourth engagement portions 746 may extend outward away from the centerline C1 and/or inward toward the centerline C1 of the therapeutic device 700.

As a result, the therapeutic device 700 described and illustrated herein is securable to the user's intromittent organ (not shown) in a comfortable manner without the need to additional securing devices, aids in promoting the flow of blood into the intromittent organ (not shown) in a natural manner, aids in helping the user (not shown) obtain and/or maintain an erection, and aids the user (not shown) in alleviating a sexual dysfunction such as but not limited to ED and/or impotence in a natural a non-pharmaceutical manner.

Figure 8:
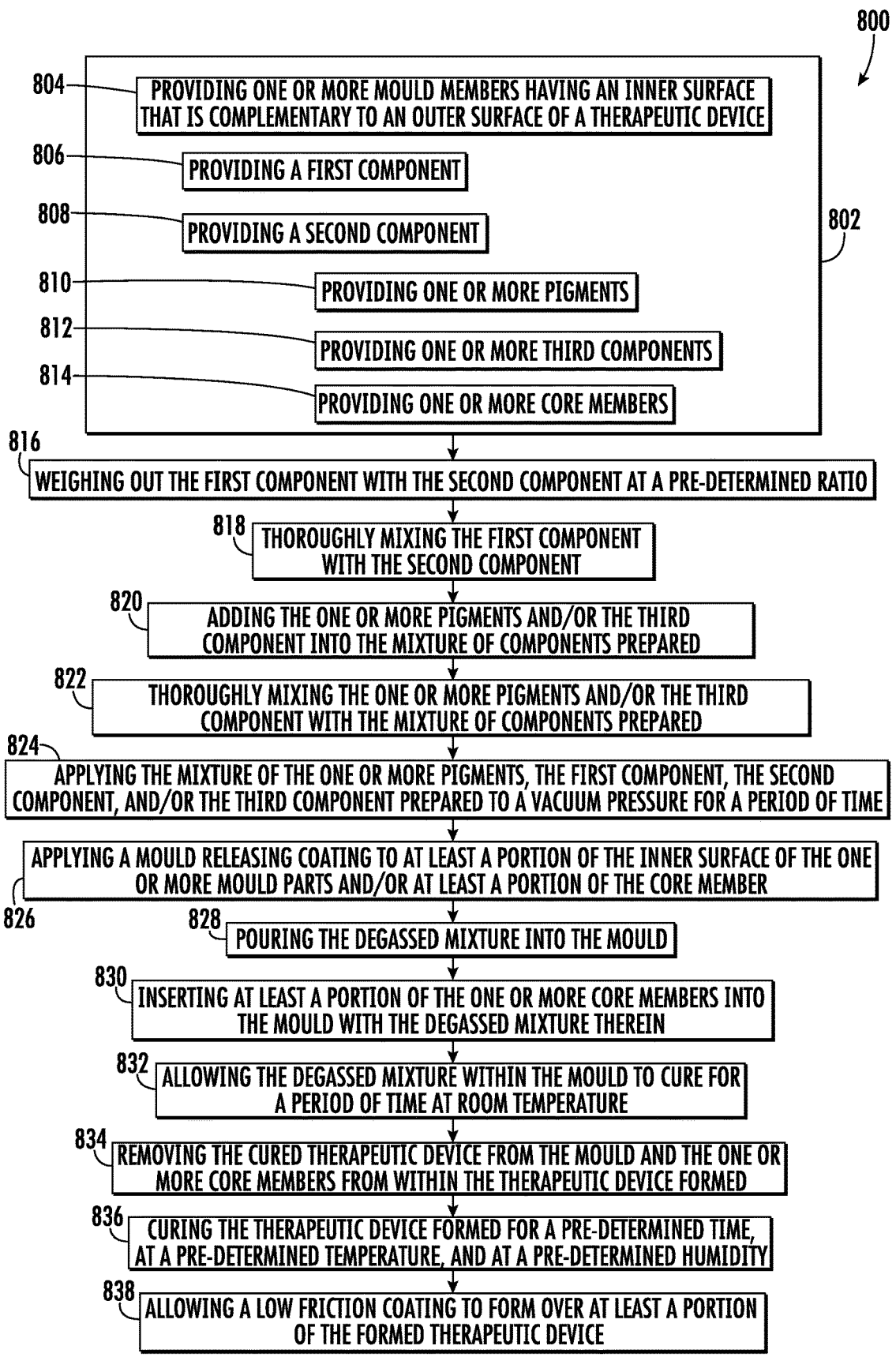
FIG. 8 is a flow chart illustrating the method of making a therapeutic device.

FIG. 8 is a flow chart illustrating method of making a therapeutic device 800 according to an embodiment of the disclosure. The method 800 includes a providing step 802 where one or more of the components needed to create or form the therapeutic device 10, 200, 300, 400, 500, 600, and/or 700 described and illustrated in relation to FIGS. 1-7 of the disclosure. As illustrated in FIG. 8 of the disclosure and as a non-limiting example, the providing step 802 may include the step of providing one or more mould members 804. The one or more mould members (not shown) may have an inner surface (not shown) that is complementary to at least a portion of the outer surface 104 of the therapeutic device 100, 200, 300, 400, 500, 600, and/or 700. As a result, it is therefore to be understood that the one or more mould members (not shown) may be selectively connected to each other to form a single inner surface that defines the outer surface 104 of the therapeutic device 100, 200, 300, 400, 500, 600, and/or 700.

Additionally, the providing step 802 may include the step of providing a first component 806 and/or providing a second component 808. The first component 806 and/or the second component 808 may make up the composition of the material of the first body portion 102 and/or the second body portion 202 of the therapeutic device 100, 200, 300, 400, 500, 600, and/or 700. It is within the scope of this disclosure and as a non-limiting example that the first component 806 may have a Shore A hardness in a range of about 00 to about 22 and the second component 808 may have a Shore A hardness in a range of about 00 to about 30. As a non-limiting example, the first component 806 and/or the second component 808 may be a Platinum Set Silicone manufactured by Smooth-On, Inc.

As illustrated in FIG. 8 and as a non-limiting example, the providing step 802 may include the step of providing one or more pigments 810. The one or more pigments 810 provided may be mixed with at least one of the first and second components 806 and 808 provided in order to obtain the desired color and/or external look for the therapeutic device 100, 200, 300, 400, 500, 600, and/or 700.

The providing step 802 may further include the step of providing one or more third components 812. The one or more third components 812 provided may aid in forming at least a portion of the one or more coatings 134 on the body portion 102 of the therapeutic device 100, 200, 300, 400, 500, 600, and/or 700. As previously discussed herein, the one or more third components 812 may be mixed with the first component 806, the second component 808, and/or the one or more pigments 810 and impregnated into the material of the body portion 102 of the therapeutic device 100, 200, 300, 400, 500, 600, and/or 700 and/or applied to the outer surface 104 of the therapeutic device 100, 200, 300, 400, 500, 600, and/or 700. In certain embodiments, the one or more third components 812 may be a surface tension diffuser material that causes a reduction in surface tension of the body portion 102 of the therapeutic device 100, 200, 300, 400, 500, 600, and/or 700. It is within the scope of this disclosure and as a non-limiting example that the one or more third components 812 may be a derived from at least one of a durian fruit, a tree nut, and musk thistle seed.

Additionally, the providing step 802 may include the step of providing one or more core members 814. An outer surface (not shown) of the one or more core members (not shown) may have a shape that is complementary to the surface 126, 326, 426, 526, and/or 220 defining the receiving portion 118, 218, 318, 418, 518, 618, and/or 718 of the first and/or second body portions 102 and/or 202. The one or more core members (not shown) may be selectively inserted within a void (not shown) in the one or more mould members (not shown). Additionally, the one or more core members (not shown) may be selectively connectable to and/or registerable relative to the one or more mould members (not shown) in order to ensure that the receiving portions 118, 218, 318, 418, 518, 618, and/or 718 are formed in their preferred locations within the first and/or second body portions 102 and/or 202 of the therapeutic device 100, 200, 300, 400, 500, 600, and/or 700. It is within the scope of this disclosure and as a non-limiting example that the one or more core members may be formed by using one or more machining processes, one or more milling processes, using one or more moulding processes and/or one or more 3-D printing processes.

Once the needed components have been provided during the providing step 802, the first component 806 and the second component 808 may be weighed out into a pre-determined ratio relative to each other 816. The pre-determined ratio 816 may be based on the desired Shore A hardness for the first and second body portions 102 and 202 of the therapeutic device 100, 200, 300, 400, 500, 600, and/or 700. It is within the scope of this disclosure and as a non-limiting example that the pre-determined ratio 816 may be a 50:50 mix of the first component 806 relative to the second component 808. Additionally, it is within the scope of this disclosure and as a non-limiting example that the desired Shore A hardness for the first and second body portions 102 and 202 may be approximately 00-24 to approximately 00-28, respectively.

Once the first and second components have been weighed out at the pre-determined ratio 816, the first and second components may be thoroughly mixed 818 with each other. The first and second components may be thoroughly mixed 818 with each other for a pre-determined time at room temperature. This aids in ensuring that the first and second components 806 and 808 are thoroughly mixed with each other to form a substantially homogeneous mixture before the mixture hardens or cures.

After the first and second components have been thoroughly mixed 818 with each other, one or more pigments and/or one or more third components may be added 820 to the mixture of the first and second components 818 prepared. Once the one or more pigments and/or one or more third components have been added 820 to the mixture 818, the one or more pigments and/or third components may be mixed 822 with the mixture of the first and second components 818 prepared. It is within the scope of this disclosure and as a non-limiting example that the mixture 822 may be a substantially homogeneous mixture or a heterogeneous mixture in order to provide the intended outward look for the therapeutic device 100, 200, 300, 400, 500, 600, and/or 700.

The mixture 822 prepared including the first component 806, the second component 808, and/or the one or more pigments 810, and/or the third components 812 to a pre-determined vacuum pressure for a pre-determined amount of time 824. By applying the mixture 822 prepared to the pre-determined vacuum pressure for the pre-determined amount of time 824, it aids in removing all or substantially all of the air bubbles (or gas bubbles) formed within the mixture 822 during the mixing processes. This may be known as a degassing process. By removing all or substantially all of the air bubbles (or gas bubbles) from within the mixture 822 it aids in increasing the overall life and durability of the therapeutic device 100, 200, 300, 400, 500, 600, and/or 700. If the air bubbles (or gas bubbles) formed within the mixture 822 were to remain within the final therapeutic device 100, 200, 300, 400, 500, 600, and/or 700 formed, the air bubbles (or gas bubbles) tend to create failure locations that reduce the overall life and durability of the therapeutic device 100, 200, 300, 400, 500, 600, and/or 700 formed. It is within the scope of this disclosure and as a non-limiting example that the vacuum pressure may be from approximately 25 bar to approximately 30 bar. Additionally, it is within the scope of this disclosure and as a non-limiting example that the mixture 822 may be subjected to the vacuum pressure for approximately 2 minutes to approximately 4 minutes.

Before the degassed mixture 824 is poured into the mould 828 and the one or more core members are inserted into the mould and the degassed mixture 830, a releasing agent may be applied 826 to the inner surface (not shown) of the one or more mould members (not shown) and/or to the outer surface (not shown) of the one or more core members (not shown). The releasing agent applied 826 may be a mould releasing agent that aids in the removal of the first body portion 102 and/or second body portion 202 from the one or more mould members 804 without damaging the outer surface 104 of the first and/or second body portions 102 and/or 202 of the therapeutic device 100, 200, 300, 400, 500, 600, and/or 700 formed. Additionally, the releasing agent applied 826 may aid in the removal of the one or more core members 814 from within the receiving portions 118, 218, 318, 418, 518, 618, and/or 718 of the first and/or second body portion 102 and/or 202 without damaging the functionality and shape of the receiving portions 118, 218, 318, 418, 518, 618, and/or 718 of the therapeutic device 100, 200, 300, 400, 500, 600, and/or 700 formed.

Once the degassed mixture 824 is poured 828 into the one or more mould members (not shown), at least a portion of the one or more core members 814 is inserted therein 830. The degassed mixture 824 is then allowed to cure to a pre-determined amount of time at room temperature 832. This allows the degassed mixture 824 to be cure or harden and form the therapeutic device 100, 200, 300, 400, 500, 600, and/or 700. It is within the scope of this disclosure and as a non-limiting example that the degassed mixture 824 may be allowed to cure 832 within the one or more mould members 804 for approximately 10 hours to approximately 18 hours.

After the degassed mixture 824 has been cured 832, the formed therapeutic device 100, 200, 300, 400, 500, 600, and/or 700 may be removed 834 from the one or more moulds 804 and the one or more core members 814 may be removed 834 from within the therapeutic device 100, 200, 300, 400, 500, 600, and/or 700.

In the event that the therapeutic device 100, 200, 300, 400, 500, 600, and/or 700 formed is intended or desired to include one or more coatings 134 thereon a further curing step 836 may be performed. The further curing step 836 may include subjecting the cured 832 therapeutic device 100, 200, 300, 400, 500, 600, and/or 700 to a pre-determined temperature, for a pre-determined amount of time, and/or at a pre-determined humidity. This allows for the formation of the one or more coatings 134 on the therapeutic device 100, 200, 300, 400, 500, 600, and/or 700 formed. It is within the scope of this disclosure and as a non-limiting example that the pre-determined time for the further curing step 836 may be from approximately 22 hours to approximately 50 hours. Additionally, it is within the scope of this disclosure and as a non-limiting example that the pre-determined percent humidity for the further curing step 836 may be from approximately 25 to approximately 45%. Furthermore, it is within the scope of this disclosure and as a non-limiting example that the pre-determined temperature for the further curing step 836 may be from approximately 75° F. to approximately 90° F.

During the further curing step 836, the one or more coatings 134 may be allowed 838 for form on at least a portion of the outer surface 104 of the first body portion 102 of the therapeutic device 100, 200, 300, 400, 500, 600, and/or 700 formed.

EXAMPLES

Example #1

The therapeutic device 100, 200, 300, 400, 500, 600, and/or 700 formed was provided to a first test subject suffering from a diagnosed sexual dysfunction such as but not limited to ED and/or impotence. The first test subject was diagnosed with the sexual dysfunction as a result of a surgery intended to enlarge the user's intromittent organ. By utilizing the therapeutic device 100, 200, 300, 400, 500, 600, and/or 700, the first test subject was able to maintain an erection of his intromittent organ. Additionally, the therapeutic device 100, 200, 300, 400, 500, 600, and/or 700 was successfully securable to at least a portion of the user's intromittent organ allowing for to engage in sexual relations with his partner.

Example #2

The therapeutic device 100, 200, 300, 400, 500, 600, and/or 700 formed was provided to a second test subject suffering from a diagnosed sexual dysfunction such as but not limited to ED and/or impotence. The second test subject was diagnosed with the sexual dysfunction as a result of a side-effect to prescription drugs prescribed to alleviate a cardiac issue identified. By utilizing the therapeutic device 100, 200, 300, 400, 500, 600, and/or 700, the second test subject was able to maintain an erection of his intromittent organ. Additionally, the therapeutic device 100, 200, 300, 400, 500, 600, and/or 700 was successfully securable to at least a portion of the user's intromittent organ allowing for the user to engage in sexual relations with his partner.

It is to be understood that the various embodiments described in this specification and as illustrated in the attached drawings are simply exemplary embodiments illustrating the inventive concepts as defined in the claims. As a result, it is to be understood that the various embodiments described and illustrated may be combined to from the inventive concepts defined in the appended claims.

In accordance with the provisions of the patent statutes, the present invention has been described to represent what is considered to represent the preferred embodiments. However, it should be note that this invention can be practiced in other ways than those specifically illustrated and described without departing from the spirit or scope of this invention.

What is claimed is:

1. A therapeutic device, comprising:
  a first body portion having a first end, a second end, a first end portion, a second end portion, and an intermediate portion interposed between the first and second end portions; and
  a receiving portion is at least partially defined by the first body portion from at least a portion of the first end, wherein at least a portion of an inner surface of the receiving portion is configured to be in direct facing contact with an object at least partially disposed within the receiving portion to provide at least a partial vacuum between the at least a portion of the inner surface of the receiving portion and at least a portion of the object at least partially disposed within the receiving portion of the therapeutic device;
  wherein the inner surface of the receiving portion is a sole device of the first body portion adapted to provide the partial vacuum;
  wherein the first body portion is symmetrical about a longitudinal axis between the first end and the second end,
  wherein an opening in the first end is the sole opening in the first body portion, wherein the opening is adapted to selectively receive the object,
  wherein the inner surface angles away from the longitudinal axis at a substantially constant angle from the opening to the second end portion,
  wherein a wall thickness of the first body portion between the inner surface of the receiving portion and an outer surface of the first body portion is variable across a length of the therapeutic device and the wall thickness is sufficient to retain the shape of the first body portion.

2. The therapeutic device of claim 1, wherein the first body portion is formed from at least one of a polymeric composition, an elastomeric composition, a silicone composition, a siloxane composition, a poly-siloxane composition, and a biomimetic composition.

3. The therapeutic device of claim 1, wherein the angle of the inner surface of the receiving portion is less than 45°.

4. The therapeutic device of claim 1, wherein the second end portion is configured to receive at least a portion of a fluid discharged from the object.

5. The therapeutic device of claim 1, wherein at least one coating is formed on an outer surface of and impregnated into the at least a portion of the first body portion.

6. The therapeutic device of claim 1, further comprising a second body portion disposed in the receiving portion.

7. The therapeutic device of claim 6, wherein the second body portion is formed from at least one of a polymeric composition, an elastomeric composition, a silicone composition, a siloxane composition, a poly-siloxane composition, and a biomimetic composition.

8. The therapeutic device of claim 6, wherein the second body portion extends at an angle relative to a centerline of the therapeutic device.

9. The therapeutic device of claim 8, wherein the angle of the second body portion is less than 45°.

10. The therapeutic device of claim 1, wherein at least a portion of the first end portion includes at least one third portion.

11. The therapeutic device of claim 10, where a distance between a centerline of the therapeutic device and an inner surface of the at least one third portion is less than a distance from the centerline of the therapeutic device and the inner surface of the receiving portion.

12. A therapeutic device, comprising:
   a first body portion having a first end, a second end, a first end portion, a second end portion, and an intermediate portion interposed between the first and second end portions; and
   a receiving portion is at least partially defined by the first body portion, wherein at least a portion of an inner surface of the receiving portion is configured to be in direct facing contact with an object at least partially disposed within the receiving portion to exert an amount of suction force on at least a portion of the object at least partially disposed within the receiving portion of the therapeutic device,
   wherein an opening in the first end is the sole opening in the first body portion, wherein the opening is adapted to selectively receive the object,
   wherein the inner surface angles away from the longitudinal axis at a substantially constant angle from the opening to the second end portion,
   wherein a wall thickness of the first body portion between the inner surface of the receiving portion and an outer surface of the first body portion is variable across a length of the therapeutic device and the wall thickness is sufficient to retain the shape of the first body portion.

13. The therapeutic device of claim 12, wherein the amount of suction force exerted on the object facilities a flow of a fluid into the object.

14. A method of forming a therapeutic device, comprising the steps of:
   providing one or more mould members, a first component, a second component, and at least one core member;
   weighing an amount of the first component and an amount of the second component to produce a pre-determined ratio;
   mixing the amount of the first component with the amount of the second component to form a mixture thereof; and
   allowing the mixture of the first component and the second component to cure to form a therapeutic device, wherein the therapeutic device has formed therein a first end,
   a second end, a first end portion, a second end portion, and a receiving portion having an inner surface, wherein at least a portion of the inner surface of the receiving portion is configured to selectively generate at least a partial vacuum, wherein said inner surface is placed in direct facing contact with an object to be inserted into an only opening in the receiving portion to create the partial vacuum;
   wherein the inner surface angles away from a longitudinal axis at a substantially constant angle from the opening to the second end portion,
   wherein a wall thickness of the first body portion between the inner surface of the receiving portion and an outer surface of the first body portion is variable across a length of the therapeutic device and the wall thickness is sufficient to retain the shape of the first body portion.

* * * * *